(12) United States Patent
Kim et al.

(10) Patent No.: US 6,583,293 B1
(45) Date of Patent: Jun. 24, 2003

(54) PREPARATION METHOD OF 3-NITRO-1,2,4-TRIAZOL-5-ONE BY A PROCESS MINIMIZING HEAT GENERATION DURING CRYSTALLIZATION

(75) Inventors: Hyung Sik Kim, Daejeon (KR); Eun Mee Goh, Daejeon (KR); Bang Sam Park, Daejeon (KR)

(73) Assignee: Agency for Defense Development (KR)

( * ) Notice: Subject to any disclaimer, the term of this patent is extended or adjusted under 35 U.S.C. 154(b) by 0 days.

(21) Appl. No.: 10/195,056

(22) Filed: Jul. 12, 2002

(51) Int. Cl.⁷ ............................................. C07D 249/14
(52) U.S. Cl. ................................................... 548/263.8
(58) Field of Search ........................................ 548/263.8

(56) References Cited

U.S. PATENT DOCUMENTS 4,733,610 A * 3/1988 Lee et al. .................... 102/332

H861 H * 12/1990 Collignon et al. ......... 548/263.8

OTHER PUBLICATIONS

Alain Becuwe and A. Delclos/Propellants, Explosives, Pyrotechnics 18, 1–10(1993), "Low–Sensitivity Explosive Compounds for Low Vulnerability Warheads".

* cited by examiner

*Primary Examiner*—Patricia L. Morris
(74) *Attorney, Agent, or Firm*—Scully, Scott, Murphy & Presser

(57) ABSTRACT

A preparation method of 3-nitro-1,2,4-triazol-5-one using 1,2,4-triazol-5-one (TO) and mixed acid through a stable nitration process which can minimize a large exotherm and associated frothing problem during crystallization by inducing a crystal nucleus to be generated at a low temperature of 35° C.–45° C.

1 Claim, 3 Drawing Sheets

PREPARATION METHOD OF 3-NITRO-1,2,4-TRIAZOL-5-ONE BY A PROCESS MINIMIZING HEAT GENERATION DURING CRYSTALLIZATION

BACKGROUND OF THE INVENTION

1. Field of the Invention

The present invention relates to a preparation method of 3-Nitro-1,2,4-triazol-5-one (hereinafter, referred to as "NTO") from 1,2,4-triazol-5-one (hereinafter, referred to as "TO").

2. Description of the Background Art

Research into NTO to apply as an insensitive high explosives had been confidentially performed in early 1980s in France. A result of research that NTO was applied to explosives was disclosed in U.S. Pat. No. 4,733,610 in 1987 by Lee et al. in Los Alamos national institute (USA). Since then, researches for applying to the insensitive explosives have been performed.

There are many processes for synthesizing NTO. Among them, the most generalized method is a two-step reaction which undergoes reactions as shown in below schemes 1 and 2, and in which semicarbazide. HCl is used as a starting material.

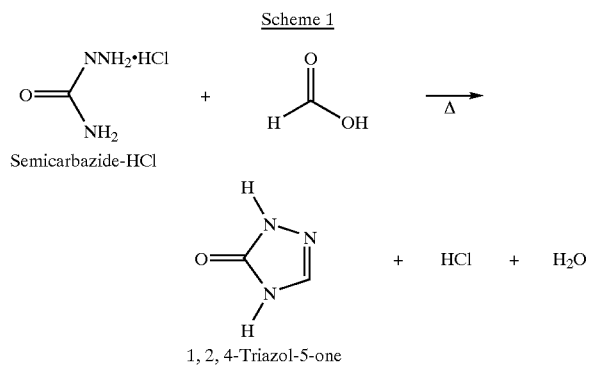

1, 2, 4-Triazol-5-one

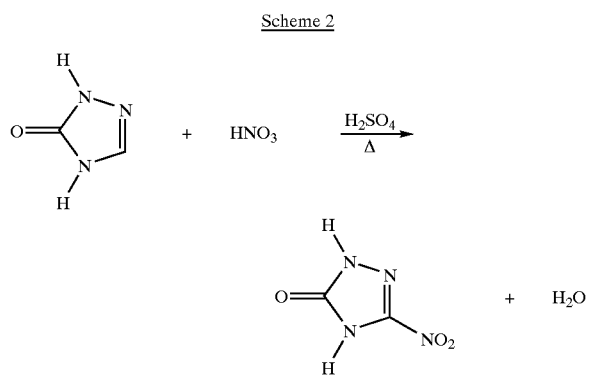

There have been known many processes for preparing NTO from the TO as follows:

(1) The process suggested by Lee et al. in the U.S. Pat. No. 4,733,610 is as follows. TO is added to 70% nitric acid, and then the mixture was heated to the temperature of 55° C.–60° C. where a exothermic reaction is started. The reactor is then allowed to self heated until the reaction is complete. However, in this process, yield is only 65% based on TO, and it is disadvantages in that it is impossible to ensure safety because the temperature can not be controlled.

(2) Collignon et al. discloses a process which improves the problems of the U.S. Pat. No. 4,733,610 in US Statutory Invention Registration No. H861 (Dec. 4, 1990). In this process, temperature of 70% nitric acid is maintained at 65° C.–70° C., dried TO is added gradually into the nitric acid, and then the temperature is maintained until the reaction is completed. This reference describes that it takes 2–3 hours for this process, and the yield is 90% based on TO. In addition, they also suggested a successive process in which the supply of TO and 70% nitric acid to a reactor where the temperature is maintained at 65° C.–70° C. at a predetermined rate is carried out simultaneously with discharge at a same speed, and reported that the yield was 83% based on TO. However, since this process is performed at a high temperature, there are problems in that a rapid exothermic reaction occurs in the crystallization step of NTO, and subsequently, the problem of frothing of the reaction mixture is encountered. Especially, in UK Laid-open Patent Publication No. 2218986, it has been reported that the use of solid TO can lead to the formation of "hot spots" at the solid-liquid interface, and to a reduced yield of the desired NTO.

(3) European Patent application No. 210811 discloses a process to solve the problems of the above described exothermic reaction and foaming. In this process, 98% nitric acid and TO are mixed at a low temperature of 5° C.–10° C., followed by a three hour holding period at ambient temperature, followed by quenching with water at 0° C. holding for 12 hours. However, this process is clearly very much time consuming. In addition, 98% nitric acid is relatively expensive starting material.

In the nitration process, the reaction rate is generally increased as the reaction temperature is higher, and therefore, the processing time is shortened. Accordingly, the conventional methods mainly use a high temperature process.

In case of NTO synthesis, it has been known that the highest yield is also achieved at the temperature range of 60° C.–70° C. However, in the process for preparing NTO, the initially generated NTO is dissolved in the reaction medium, and then the crystal is deposited at one time when the reaction medium is over-saturated as the reaction is proceeded. The amount of heat generated in a reactor is increased in a moment due to the heat generated during crystallization, and a large amount of foams are generated at the same time. Although such rapid exothermic reaction can be controlled with an automated cooling device, it is more desirable that a stable process is provided.

SUMMARY OF THE INVENTION

Therefore, an object of the present invention is to provide a preparation method of NTO with stability and high yield by solving problems of conventional methods such as a large exotherm and associated frothing during crystallization.

The object of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate Examples of the invention and together with the description serve to explain the principles of the invention.

In the drawings.

DETAILED DESCRIPTION OF THE PREFERRED EMBODIMENTS

Reference will now be made in detail to the preferred embodiments of the present invention and examples of which are illustrated in the accompanying drawings.

In the present invention, a heat generation in the NTO synthetic process was analyzed precisely using a 2L of Reaction Calormetry (Mettler RC-1). From this, it was founded that the amount of heat generated during crystallization is increased as the temperature where the NTO crystal is generated is higher (see Comparative Examples 1–3). Accordingly, the present invention provides a new process that can minimize the heat generation during crystallization in the process of preparing NTO by inducing the NTO crystal to be generated at a lower temperature, and therefore, can solve the problems of conventional art such as a large exotherm and frothing.

According to an embodiment of the present invention, after non-dried TO, 70% nitric acid and 98% sulfuric acid are mixed, in a first step, the temperature of reactant is maintained at 35° C.–45° C. The reaction is then proceeded slowly, and it can be identified that a NTO crystal nucleus is generated after 40 minutes–1 hour. The generation of a crystal nucleus can be easily identified through a viewing window on the reactor from the moment when the color of the reaction mixture changes into yellow. After the crystal nucleus is generated, in a second step, the temperature of the reaction mixture is raised to 60° C.–70° C., to make the reaction be completed. In this step, the rate of temperature raising can be adjusted in the range of 0.1–1.0° C./min. The foaming can be minimized as the reactant is heated slowly. When the NTO synthetic process is performed through the above two steps, the actual reaction time required can be optimized within 3 hours.

In the preparation method of NTO according to the present invention, froth is not generated during generation of crystal because the reaction is carried out under a mild condition of low temperature. Furthermore, crude NTO particles generated can be maximized because crystals are generated under a condition where the degree of over-saturation of the reactants is maximum according to the crystallization theory. Even if the process according to the present invention is scaled up to 8 kg batch, the stability of process is superior to the conventional art, the filtration process can be easily performed due to the generation of large particles, and the residual amount of acid in product can be minimized.

The yield of NTO of the present invention exhibits 80–90% based on TO, and such result is similar to that of the conventional art. When the wet TO containing 10 to 15% of water, formic acid and hydrochloric acid is used, the yield is lowered as about 5% compared with when the dried TO is used.

EXAMPLES

Hereinafter, the present invention will be described in more detail with reference to the Examples, to which the present invention is not limited.

Figure 1:
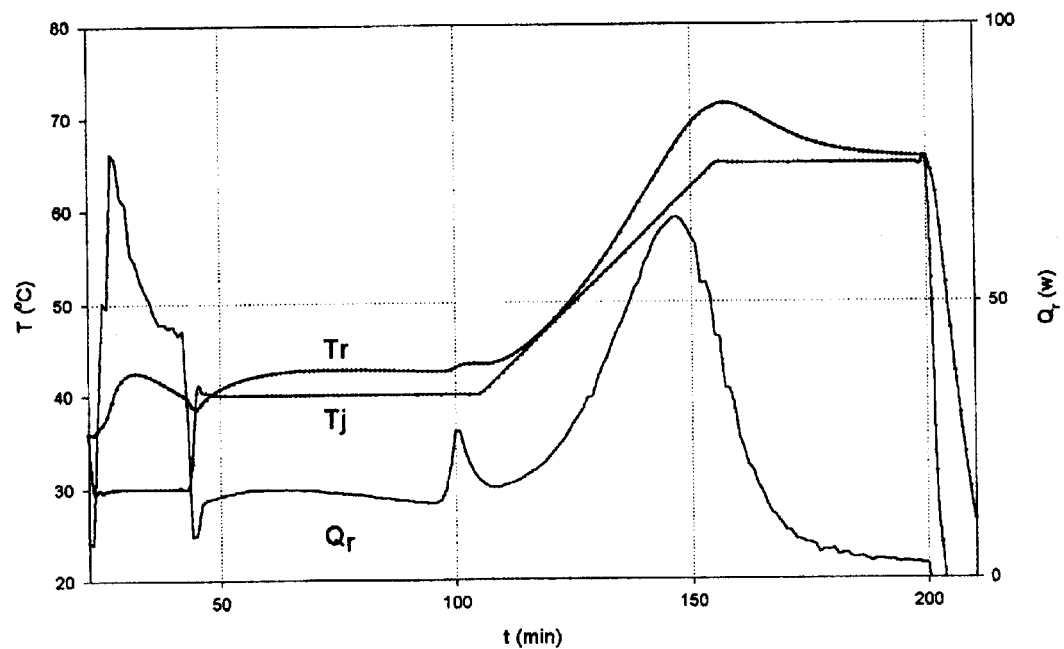
FIG. 1 exhibits a characteristic of heat generation of NTO synthetic process minimizing heat generation during crystallization according to Example 1 of the present invention (jacket-temperature controlling)
Figure 2:
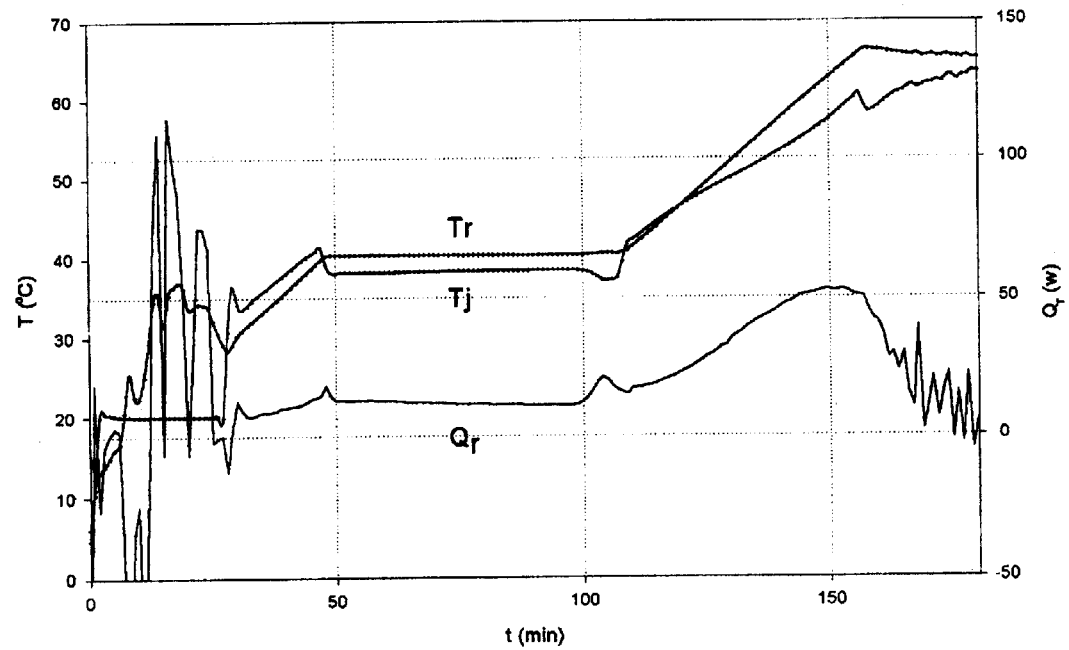
FIG. 2 exhibits a characteristic of heat generation of NTO synthetic process minimizing heat generation during crystallization according to Example 2 of the present invention (reactor temperature controlling)
Figure 3:
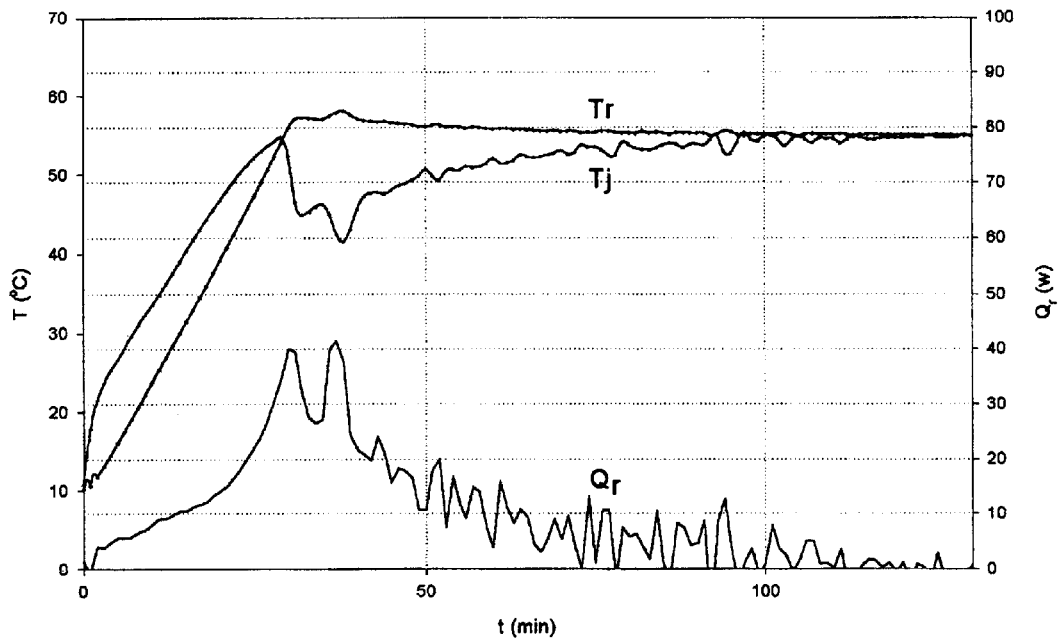
FIG. 3 exhibits a characteristic of heat generation of NTO synthetic process in the conventional batch process according to Comparative Example 1.
Figure 4:
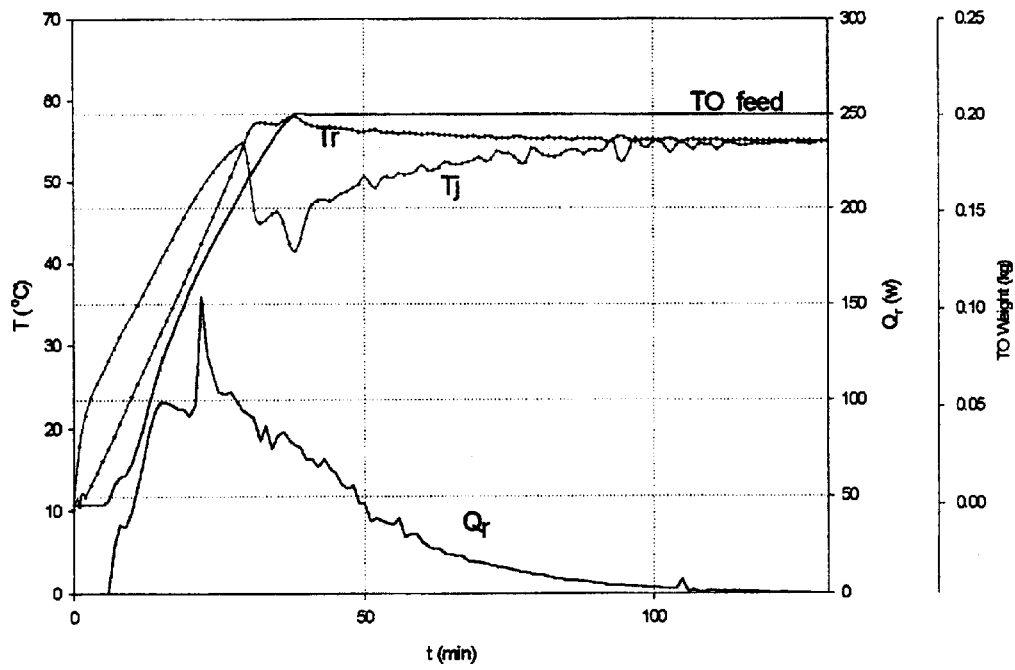
FIG. 4 exhibits a characteristic of heat generation of NTO synthetic process in the conventional TO-supplying method according to Comparative Example 2.
Figure 5:
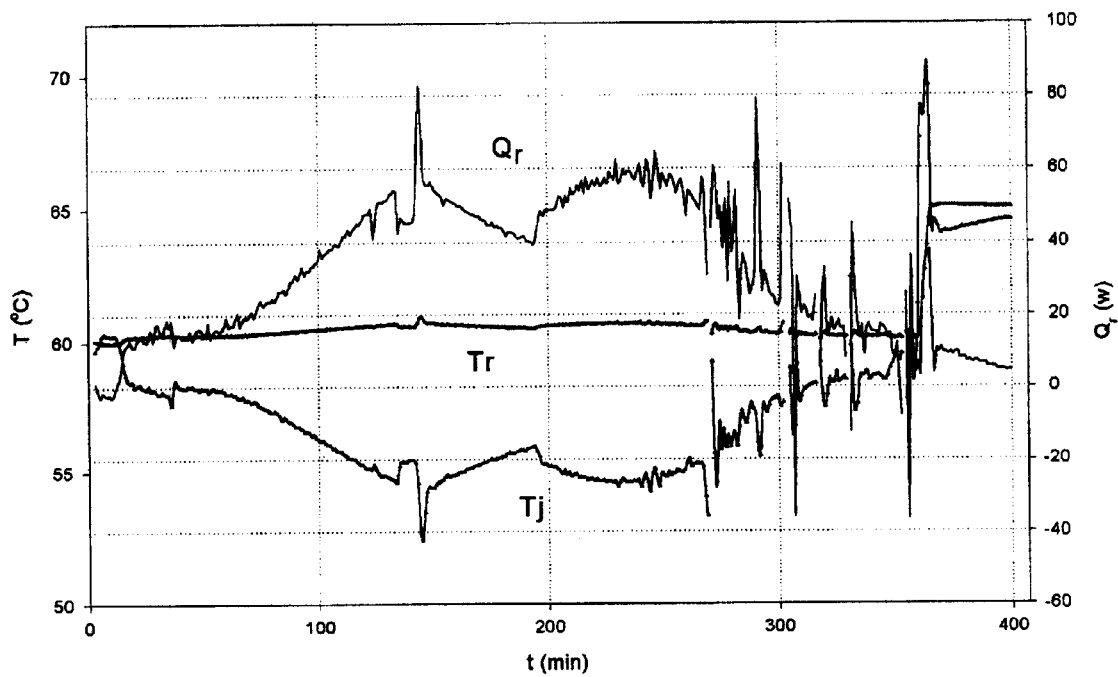
FIG. 5 exhibits a characteristic of heat generation of NTO synthetic process in the conventional conc. nitric acid-supplying method according to Comparative Example 3.

Examples 1 and 2 are NTO synthetic processes by the process minimizing heat generation during crystallization according to the present invention. Comparative Examples 1 through 3 are conventional NTO synthetic processes. Results of the Examples and Comparative Examples are shown in FIGS. 1 through 5, respectively. The definitions of terms used in Figures are as follows.

Tr: temperature of reactor (° C.)

Tj: temperature of jacket (° C.)

Qr: heat generation ratio (W)

Example 1

Process Minimizing Heat Generation During Crystallization by Controlling the Temperature of Jacket While the temperature of a jacket is maintained at 25° C., non-dried TO (100 g based on dried weight) of room temperature and 136 g of 98% sulfuric acid were gradually put into a reactor. 476 g of 70% nitric acid was supplied into the reactor for 20 minutes while temperature of the reactant was maintained at 25° C. When nitric acid supply was finished, the temperature of jacket was raised into 35° C.–45° C., and then the temperature was maintained for 40 minutes–1 hour, to generate a NTO crystal nucleus. The jacket was then heated at a temperature rising rate of 0.1° C./min–1.0° C./min, so as to the temperature of the jacket be 55° C. The reaction mixture was then allowed to naturally rise the temperature to 60° C.–70° C., which was the highest temperature, and then 30 minutes later, the reaction was finished. After the reaction was completed, the reaction mixture was cooled down to 5–10° C., and then the product was collected by filtering the reaction mixture through a filter or a filter cloth.

Example 2

Process Minimizing Heat Generation Druing Crystallization by Controlling the Temperature of Reactant While the temperature of jacket was maintained at 10° C., non-dried TO (100 g based on dried weight) of room temperature and 110 g of 98% sulfuric acid were gradually put into a reactor. 476 g of 70% nitric acid was supplied into the reactor for 20 minutes while the temperature of reactant was maintained at 20° C. When nitric acid supply was finished, the temperature of jacket was raised into 35° C.–45° C., and then the temperature was maintained for 40 minutes–1 hour, to generate a NTO crystal nucleus. The jacket was then heated at a rate of 0.1–1.0° C./min, so as to the temperature of the jacket be within 60–70° C. The reaction was then continued until the heat of reaction became below 3 W, or for one and a half hours after the crystal nucleus was generated and thereby the exothermic reaction was started. After the reaction was completed, the product was collected in the same manner as in Example 1.

Comparative Example 1

Batch Process

While the temperature of jacket was maintained at 10° C., non-dried TO (100 g based on dried weight) of room temperature and 110 g of 98% sulfuric acid were gradually put into a reactor. 476 g of 70% nitric acid was pumped into the reactor for 20 minutes after the temperature of reactant was maintained at 10° C. When nitric acid supply was finished, temperature of the reaction mixture was raised to 55° C. by heating at a rate of 1° C./min, and then the reaction was continued until a temperature difference between the reactor and the jacket became 0.1° C. After the reaction was completed, the product was collected in the same manner as in Example 1.

Comparative Example 2

TO Supply Method

While the temperature of jacket was maintained at 10° C., 110 g of 98% sulfuric acid and 476 g of 70% nitric acid were gradually put into a reactor. The temperature of reactant was then raised to be 55° C. by heating at a rate of 1° C./min. While the temperature of reactant was maintained at 55° C., dried TO was supplied into the reactor at a rate of 0.5–5 g/min. The reaction was then continued until the temperature difference between the reactor and the jacket became 0.5° C. After the reaction was completed, the product was collected in the same manner as in Example 1.

Comparative Example 2 is one of representative conventional preparation methods of NTO. In this process, generated NTO was dissolved in the reaction medium and oversaturated until no less than 70% of TO was supplied, and at the moment, the crystals were deposited and thereby abrupt exothermic feature was observed. Such feature can be identified in FIG. 4.

Comparative Example 3

Conc. Nitric Acid Supply Method

While the temperature of jacket was maintained at room temperature, non-dried TO (100 g based on dried weight) of room temperature, 136 g of water and 110 g of 98% sulfuric acid were gradually put into a reactor. The temperature of reactant was then raised to 60° C. at a rate of 1°/min. While the temperature of reactant was maintained at 60° C., 340 g of 98% nitric acid was supplied into the reactor at a rate of 3–5 g/min. The reaction was then continued until the temperature difference between the reactor and the jacket became 0.5° C. After the reaction was completed, the product was collected in the same manner as in Example 1.

Comparative Example 3 is one of representative conventional preparation methods of NTO. In this process, generated NTO was dissolved in the reaction medium and oversaturated until the ⅔ of conc. nitric acid was supplied, at the moment, the crystals were deposited and thereby abrupt exothermic feature was observed. Such feature can be identified in FIG. 5.

As the present invention may be embodied in several forms without departing from the spirit or essential characteristics thereof, it should also be understood that the above-described Examples are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A preparation method of 3-nitro-1,2,4-triazol-5-one comprising:

a first step of mixing non-dried 1,2,4-triazol-5-one, 98% sulfuric acid and 70% nitric acid in a reactor while the temperature is maintained at 25° C., and then raising the temperature to 35–45° C. and maintaining at the same temperature, to generate a crystal nucleus of 3-nitro-1,2,4-triazol-5-one; and a second step of completing the reaction by heating the reaction mixture to 60–70° C.

* * * * *